(12) United States Patent
Winther et al.

(10) Patent No.: US 6,930,292 B1
(45) Date of Patent: Aug. 16, 2005

(54) METHOD OF CONTROLLING THE TEMPERATURE OF A SPECIMEN IN OR ON A SOLID SUPPORT MEMBER

(75) Inventors: Lars Winther, Smorum (DK); Kim Adelhorst, Holte (DK)

(73) Assignee: Dako A/S, Glostrup (DK)

( * ) Notice: Subject to any disclaimer, the term of this patent is extended or adjusted under 35 U.S.C. 154(b) by 157 days.

(21) Appl. No.: 10/031,357

(22) PCT Filed: Jul. 21, 2000

(86) PCT No.: PCT/DK00/00417

§ 371 (c)(1),
(2), (4) Date: Jan. 17, 2002

(87) PCT Pub. No.: WO01/07890

PCT Pub. Date: Feb. 1, 2001

(30) Foreign Application Priority Data

Jul. 21, 1999 (DK) ............................... 1999 01044

(51) Int. Cl.[7] .............................................. H05B 6/10
(52) U.S. Cl. .................................. 219/635; 156/345.38
(58) Field of Search ................................ 219/635, 647, 219/201, 50; 435/440, 69.1, 173.1; 436/35; 324/300; 356/311; 216/67; 156/345.38, 345.48; 204/298.31, 298.34, 157, 44

(56) References Cited

U.S. PATENT DOCUMENTS

| | | | |
|---|---|---|---|
| 4,401,625 A | 8/1983 | Willay et al. ................. 422/50 |
| 4,731,335 A | 3/1988 | Brigati ........................ 436/180 |
| 5,023,187 A | 6/1991 | Koebler et al. ............. 436/180 |
| 5,068,091 A | 11/1991 | Toya ........................... 422/99 |
| 5,232,667 A | 8/1993 | Hieb et al. ............... 422/82.04 |
| 5,244,787 A | 9/1993 | Key et al. ..................... 435/7.9 |
| 5,338,358 A | 8/1994 | Mizusawa et al. .......... 118/401 |
| 5,534,231 A * | 7/1996 | Savas .......................... 216/67 |
| 5,556,501 A * | 9/1996 | Collins et al. ......... 156/345.38 |
| 5,643,246 A * | 7/1997 | Leeb et al. ............... 604/890.1 |
| 5,653,885 A * | 8/1997 | Jameson et al. ............ 210/634 |

FOREIGN PATENT DOCUMENTS

| | | |
|---|---|---|
| DE | 19828837 A1 | 4/1999 |
| EP | 0 545 673 A1 | 6/1993 |
| WO | WO 92/01919 | 2/1992 |
| WO | WO 94/18539 | 8/1994 |
| WO | WO 94/23326 | 10/1994 |
| WO | WO 96/21142 | 7/1996 |

(Continued)

OTHER PUBLICATIONS

Patent Abstracts of Japan, vol. 7, No. 213, (Sep. 20, 1983), JP 58 112055 A, Jul. 4, 1983.

(Continued)

Primary Examiner—Quang T. Van
(74) Attorney, Agent, or Firm—Hamilton, Brook, Smith & Reynolds, P.C.

(57) ABSTRACT

A method of controlling the temperature of a biological specimen by using induction heating. The specimen is either fixed to a carrier or is in liquid form in contact with a carrier with fixed capture probes. The carrier is removably placed in proximity to a solid support member with a conducting material, and the solid support is subjected to an oscillating magnetic field. The carrier and support member are preferably a microscope slide and a cartridge, respectively.

31 Claims, 5 Drawing Sheets

FOREIGN PATENT DOCUMENTS

| WO | WO 97/03827 | 2/1997 |
| WO | WO 98/00580 | 1/1998 |
| WO | WO 99/34190 | 7/1999 |

OTHER PUBLICATIONS

Patent Abstracts of Japan, vol. 1999. No. 14, (Dec. 22, 1999), JP 11 258123 A, Sep. 24, 1999.

Patent Abstracts of Japan, vol. 1997, No. 10, (Oct. 31, 1997), JP 09 170972 A, Jun. 30, 1997.

Uncertified translation of the application cited in Patent Abstracts of Japan, vol. 1997, No. 10, (Oct. 31, 1997), JP 09 170972 A, Jun. 30, 1997 (Reference AT).

* cited by examiner

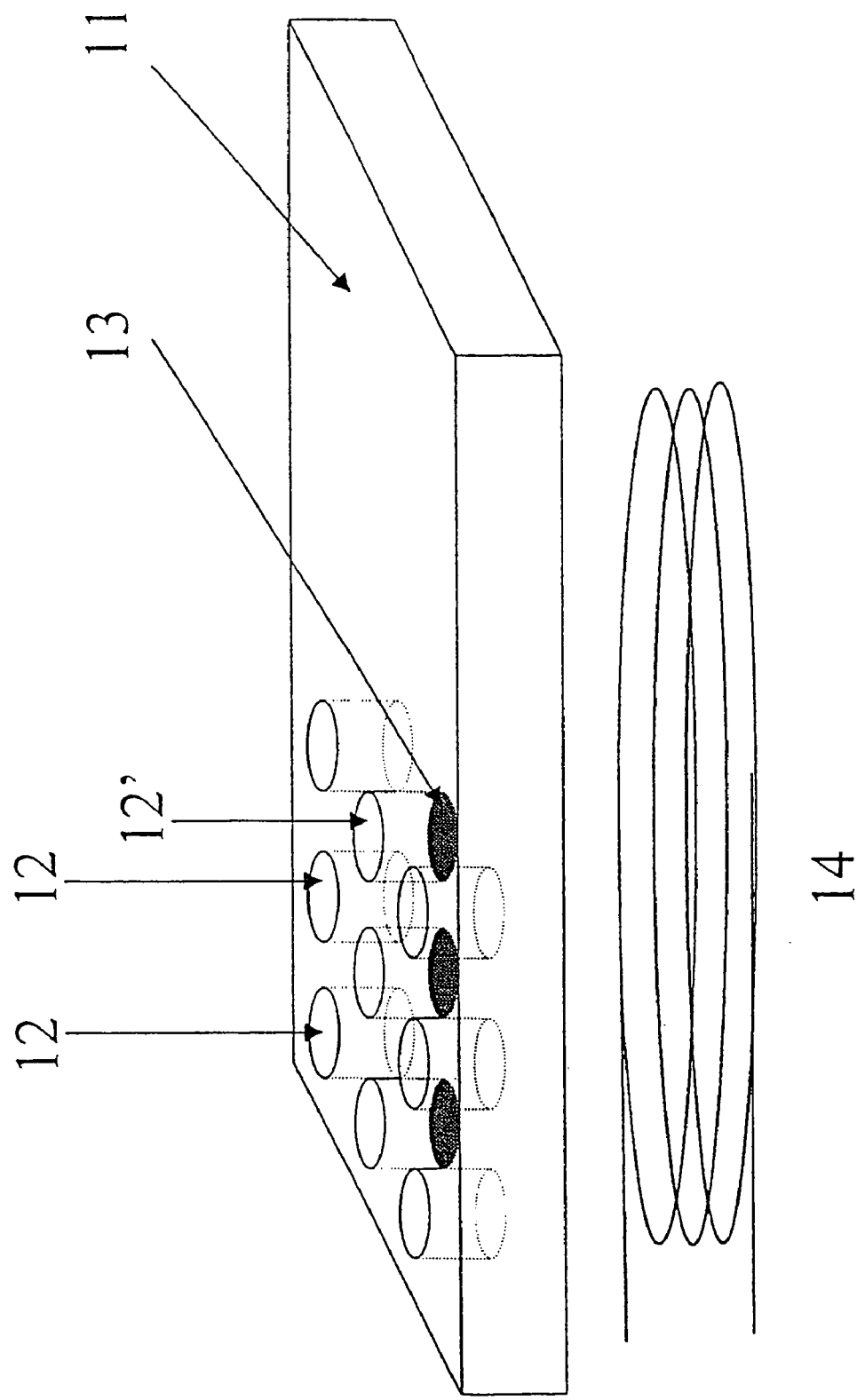

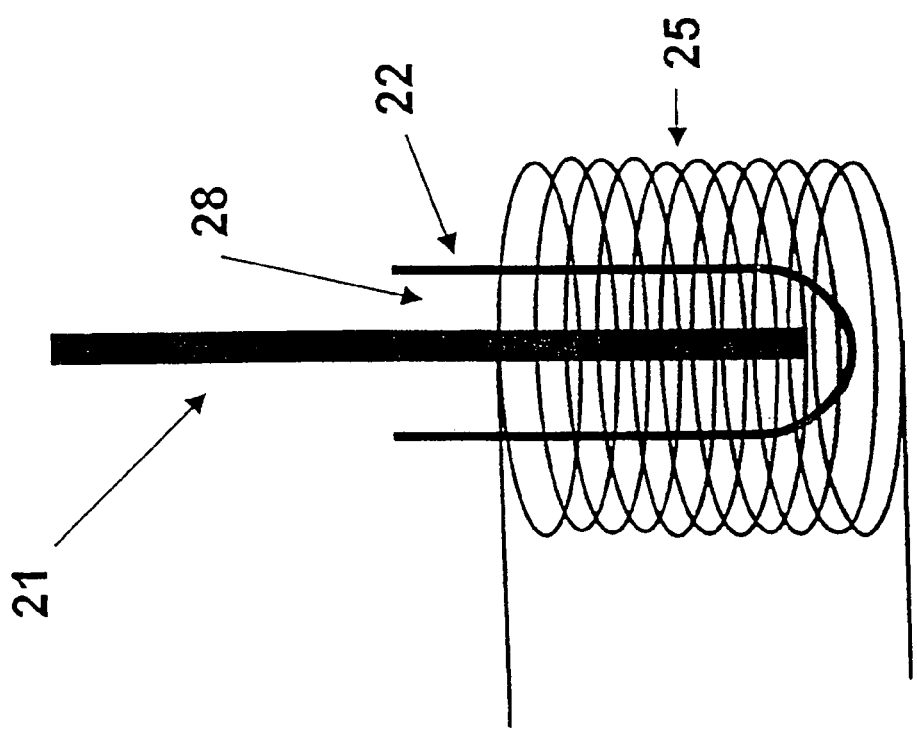

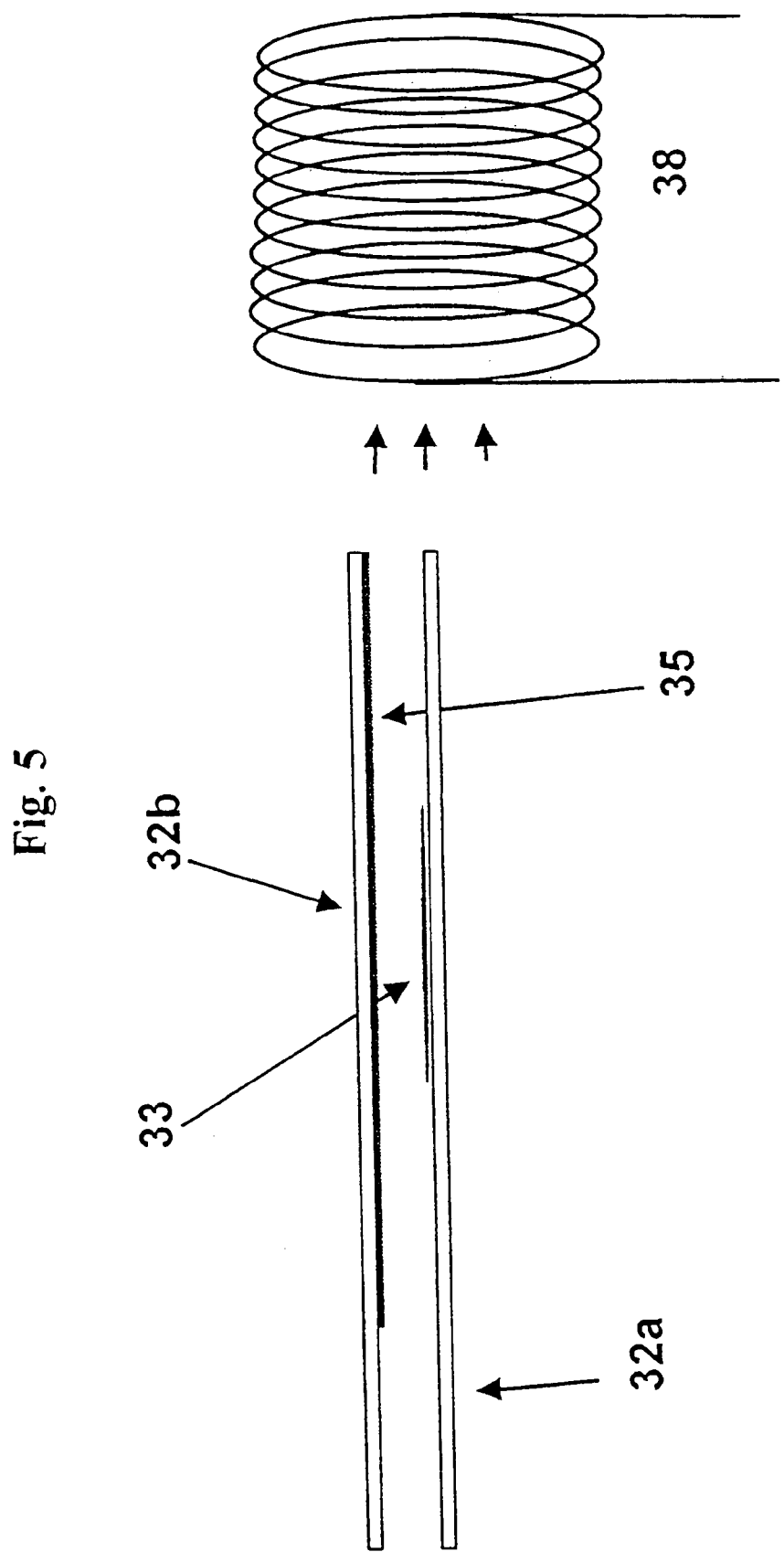

METHOD OF CONTROLLING THE TEMPERATURE OF A SPECIMEN IN OR ON A SOLID SUPPORT MEMBER

This application is the U.S. National Phase Application of International Application No. PCT/DK00/00417, filed on Jul. 21, 2000, designating the United States and published in English. The International Application claims priority to Danish Application No. PA 1999 01044, filed Jul. 21, 1999, the contents of which is incorporated herein by reference in its entirety.

The present invention relates to a method of controlling the temperature of a biological specimen during a testing step. The first aspect of the invention relates to a method wherein the specimen is fixed to a carrier such as a microscope slide or the specimen is in liquid form in contact with a carrier onto which capture probes for capturing the specimen are fixed. The carrier is placed in, on, or under a solid support member. The invention in its first aspect also relates to a solid support member, a solid support member in combination with a carrier, a solid support member in combination with an inductor and use of this solid support member. The second aspect of the invention relates to a method wherein the specimen is fixed to one or more metal containing beads or said specimen being in liquid form in contact with one or more metal containing beads onto which capture probes for capturing said specimen are fixed. The invention also relates to the beads and the use of the beads.

Throughout the world, there is an increasing demand for examining or studying samples of different types, in particular biological samples such as tissue sections, cell smears, cytospins, sections of cell blocks, molds, fungi, bacilli, fine needle aspirates and solutions containing macromolecules such as proteins, deoxyribonucleic acids and ribonucleic acids. Such samples or specimens are usually examined by placing the specimen in or on a solid carrier and subjecting the specimens to a number of treatments, where after the sample is examined using a microscope or other analytical instruments or apparatus able to detect and/or quantify the presence of particular components, e.g. specific cells, cell types, or cell components, and/or particular compounds, e.g. specific macromolecules like proteins, deoxyribonucleic acid and ribonucleic acid sequences, polysaccharides, etc., in the samples.

The solid supports or carrier generally used are microscope slides, microtiter plates or any other type of cartridges or test tubes. Normally, the specimen or the capturing probes with or without the captured specimen should remain on or in the support during the treatment procedure, and consequently it is important that the solid support is shaped depending on the type of treatment necessary for a specific test. Many assays involve a sequence of reaction steps, which should be carried out under thermostatic conditions, and/or reaction steps involving adding a reagent, allowing it to react for a persecuted time, and drying of the specimen. In other situations an assay may Involve a direct step of heat treatment.

Temperature regulations or control systems for cartridge or other solid supports are generally known in the art. In most of the systems the temperature is regulated using hot air, warm water or heat conducting elements being brought into contact with the support member.

WO 92/01919 relates to an apparatus for automatic tissue staining for immunohistochemistry, said apparatus comprising a carousel carrying a number of microscope slides, each bearing a sample. The carousel is adapted to be heated, preferably from beneath, utilising hot air or warm water.

WO 97/03827 relates to an automated slide staining system for cytology or histology specimens, said system comprising a heating station provided by a convector, conducting heat to the slides. U.S. Pat. No. 5,232,667 describes a temperature control system using conductive heater means for heating samples in cartridges.

The above described temperature systems are generally very slow, meaning that it requires a relative long time to heat the specimens. Also the fact that all of the sample holders should be contacted with the conductive heater, the water or the hot air makes the systems very cumbersome. Furthermore, heating with air or water requires large space and increases the risk of contaminating the specimen with dirt or unwanted microorganisms.

WO 94/23326 relates to a microscope slide holder used for un-form processing of the slides. In this patent publication, it is suggested that the heating step is carried out in a suitable oven. This method also requires large space, and since the heat treatment often is carried out several times during an assay, this method is not suitable in most assays. Heating an oven also requires a lot of energy, which is both expensive and unnecessary if only a few samples should be subjected to the change the temperature of the specimen.

It has also been suggested to control the temperature of specimens in or on a solid support by using infrared radiation or microwave.

U.S. Pat. No. 5,023,187 relates to a device for accelerated treatment of thin tissue specimens on microscope slides. The microscope slides are placed in a slide holder, and energy is supplied to the surface of the slides in the form of infrared radiation.

U.S. Pat. No. 5,244,787 relates to a method for retrieval of antigens from formalin-fixes, paraffin-embedded tissues and their subsequent staining by immunohistochemical techniques comprising a step of immersing the tissue sections in water and heating the water using microwave.

Working with infrared radiation and microwave requires special equipment, since exposing to infrared radiation and microwaves is injurious to health, and consequently, infrared radiation and microwave treatment should be avoided, if possible.

DE 198 28 837 discloses an ELISA test. The test includes a substrate in the form of a cylinder coated on its inner surface with a binding agent e.g. a binder for an antigen. The cylinder may be of a metal which can be heated by use of induction heat for controlling the temperature during the analysis, and which can be moved using a magnet for use in automatics analysis equipment. The cylinder may be placed in a well of a microtiter plate, and filled with liquid comprising e.g. an antigen.

In the art of carrying out quantitative tests of biological specimens it is generally preferred to fix the specimen or capture probes for the specimen onto a carrier e.g. a latex particle or a micro slide. Usually a practitioner carries out a number of different test of a biological specimen in order to get sufficient information about the patient from which the biological specimen has been taken for the doctor to make a diagnose. Some of the tests include one or more steps where heating or heat control of the specimen is necessary, other tests do not require heat control. Generally, it is a requirement from the practitioner that the specimens can be fixed on the same type of carrier irrespectively of the test to be carried out. Thus, it is not acceptable that the specimens or the capture probes for tests requiring heat control should be fixed on a metal carrier and other specimens or capture probes for tests without heat control should be fixed on e.g. glass slides, on the inner surface of a well or on latex beads.

The object of the present invention is to provide a method of controlling the temperature of a specimen, in particular a biological specimen, which method does not suffer from the drawbacks mentioned above.

A further object is to provide a method of controlling the temperature of a biological specimen fixed to a carrier or a specimen captured or about to be captures by capture probes which are fixed to a carrier such as a micro slide or latex beads or a well, which method provides a fast regulation of heat, is simple and precise, and also, at the same time is not hazardous to health.

Yet a further object is to provide equipment for carrying out such methods.

This and other objects are provided by the methods defined in the claims.

According to the method of the first aspect of the invention, the specimen to be subjected to a heat control or heat treatment is fixed to a carrier, or the specimen is in liquid form in contact with a carrier onto which capture probes for capturing said specimen are fixed, which carrier is removably placed in, on, or under a solid support member. The solid support member comprising a conducting material in that it is either totally or partially prepared from an electrically conducting material or the solid support member is equipped with an electrically conducting material by bringing one or more pieces of electrically conducting material into physical contact with the solid support member during the heat treatment step. The thickness of the electrically conducting material should preferably be sufficiently large to make it possible to generate a heat of 35° C., more preferably 50° C., even more preferably 100° C. and in certain situations even 110° C. in the electrically conducting material itself.

In principle any method of fixing a specimen or capture probes to a carrier may be used. The specimen may e.g. be fixed to the carrier by use of formalin, heat, ethanol or it may be chemically immobilized. The capture probe may preferably be fixed to the carrier by chemically immobilizing.

The capture probes may be any kind of capture probes, witch are able to capture the specimen. The capture probes may preferably be selected from the group consisting of antibodies, DNA, PNA and streptapidin. By the terms "capture probes, witch are able to capture the specimen" and "capture probes for capturing said specimen" are meant capture probes which is able to bind to the specimen or a part of the specimen. Such capturing probes normally are able to selectively recognize specific areas or markers of the specimen and bind to these, whereby the specimen or parts of the specimen will be captured.

By the term "a specimen in liquid form" is meant any liquid material comprising a specimen in solution, in dispersed or suspended form. A specimen in liquid form may e.g. be a cell suspension or a lysat.

The larger the surface area of the electrically conducting material is, the larger is the transfer of heat to the specimen. The surface area of the electrically conducting material should therefore preferably be at least 0.5 cm$^2$, more preferably at least 3 cm$^2$.

The electrically conducting material may, as indicated, be in direct contact with the specimen on the carrier. However, in most situations, it is preferred that the electrically conducting material and the specimen are not in physical contact. When the specimen are in liquid form and about to be captured by capture probes fixed to the carrier some of the area of the specimen may be in direct contact with the electrically conducting material whereas other areas is in indirect contact with the electrically conducting material. It is preferred that the electrically conducting material is in indirect contact with most or all of the specimen which means that a layer of heat conducting material is placed between the electrically conducting material and the specimen or the capture probes on the carrier, so that the electrically conducting material is in contact with the layer of heat conducting material e.g. the liquid with the sample or a reaction liquid, which heat conducting material is in direct contact with the capture probes or the specimen. The distance between the electrically conducting material and the capture probe or the specimen should, however, be sufficiently short to allow a fast heating of the specimen e.g. the specimen captured or about to be captured by the capture probes. The more heat conducting material there is between the electrically conducting material and the specimen/capturing probes, the longer it takes for the generated heat to be transmitted to the specimen.

It is preferred that the heat conducting material is either constituted by the carrier or a liquid, such as a treatment liquid e.g. an analyte or a cleaning liquid e.g. water, applied onto the specimen, or a specimen in liquid form on the carrier.

The solid support member is subjected to an oscillating magnetic field, whereby the electrically conducting material generates heat, which heat is transmitted to the specimen. The distance between the specimen or the capture probes before or after having captured the specimen, and the electrically conducting material is preferably between 5 nm and 1 cm, more preferably 10 nm and 1 mm, and even more preferably between 1 and 300 µm. The distancing material is constituted by a heat-conducting material which is defined as a substantially solid or liquid material. The distancing, heat-conducting material may be constituted by a wall of the solid support, or more preferably by the carrier or a treatment liquid for the specimen or the specimen in liquid form.

A temperature sensor may preferably be placed near to or in contact with the specimen to register the temperature. The temperature sensor may e.g. be placed in direct contact with the electrically conducting material. In a preferred embodiment an IR temperature sensor is placed sufficiently close to the electrically conducting material to measure the temperature of the electrically conducting material. In this preferred embodiment it is even more preferred that the IR temperature sensor is placed sufficiently close to a non-covered area of the electrically conducting material to measure the temperature of this area of the electrically conducting material. By "non-covered area" means that this area is not covered with a liquid or a solid mass. The temperature sensor may be a part of a regulation system regulating the oscillating magnetic field in relation to a wanted temperature of the specimen and the obtained temperature. Such regulation systems are in general known to a skilled person.

In a preferred embodiment of the present invention the temperature of the conducting material is registered by the inductor, e.g. in the form of an induction coil. By registration of the feed back from the heat induction of the conducting material placed in the oscillating magnetic field, the temperature of the electrically conducting material and thereby the temperature of the specimen placed closed thereto, e.g. in direct contact with the conducting material, can be calculated, and the oscillating magnetic field may be regulated depending on the calculated temperature and the wanted temperature of the specimen. In other words, in this embodiment the inductor has two functions, viz. to generate an oscillating magnetic field, and to measure the feed back from the heat induction of the conducting material, whereby a regulating device can determine the temperature and regulate the field strength of the oscillating magnetic field. The method of calculating the temperature of a electrically conducting material in an oscillating magnetic field by use of the feed back from the heat induction of the conducting material is known to a skilled person.

During the heat treatment step the carrier is placed in, on or under the solid support. This means that the carrier is placed in such relation to the solid support that the heat generated in the electrically conducting material of the solid support can be transferred to the specimen fixed on the carrier or the capture probes with or without captured specimen.

The solid support member may in principle be of any type, such as a microtiter plate, a cartridge, a cartridge for a microscope slide, a test tube, a probe, a membrane, or a filter.

The carrier may preferably be adapted for carrying small samples e.g. solid specimen having a size less than 3 m$^3$, preferably less than 0.1 cm$^3$, immobilized specimen immobilized onto an area of less than 5 cm$^2$, preferably less than 2 cm$^2$ or capture probes spread over an area of less than 5 cm$^2$. The carrier may preferably be a microscope slide, a particle, a bead or a probe.

The specimen is fixed to the carrier during the heat treatment step, or the capture probes is fixed to the carrier during the heat treatment step. In the latter case the specimen or parts of the specimen may be captured by the capture probe before or during the heat treatment step, which means that the specimen comes into close contact with the carrier.

Solid support members as well as carriers of the above type, but without electrically conducting materials, are well known in the art. The type of solid support member and carrier is selected depending of the type of specimen and on the type of heat control and treatment to which the specimen should be subjected.

Solid support members as described in the prior art publications U.S. Pat. No. 5,068,091, U.S. Pat. No. 5,330,358, WO publication 94/18539, WO application No. PCT/DK98/00580, WO publication No. 92/01919, WO publication No. 97/03827, U.S. Pat. No. 5,232,667, US patent No. 5,244,787, U.S. Pat. No. 5,023,187 are in general useful in the present method, when these support members are modified by equipping the support member with an electrically conducting material.

When the specimen is a solid specimen, an immobilized specimen or a specimen in liquid form, and the carrier is a particle, a bead or a probe, the solid support member may preferably be a microtiter plate, a test tube or a similar member comprising a well.

Any type of test tube or any type of microtiter plate comprising at least one or two wells may be used.

A well in a test tube or a microtiter plate may have any shape. Normally, a well is shaped as a hollow well formed by a circumferential wall having a concave or plane bottom. The well of the test tube or one of the wells of the microtiter plate comprises a conducting materiel. The conducting material may be in the form of a solid piece of electrically conducting material placed in the well or in the form of one or more solid pieces or particles of conducting material incorporated in the wall or the bottom of the well. The electrically conducting material may also be loosely placed in the well, e.g. in the form of bead shaped pieces including electrically conducting material.

If the solid support member is a microtiter plate, the microtiter plate should preferably comprise at least 5 wells and preferably at least 10 wells. All or at least a number of the wells, e.g. every second or third of the wells, may preferably be equipped with electrically conducting materials. The amount and type of electrically conducting materials in each well, or incorporated in the wall or the bottom of each well may vary from each other. These embodiments are particularly preferred when pieces of electrically conducting material are loosely placed in the wells. By using different pieces of electrically conducting material i.e. pieces of electrically conducting material having different surface areas, the temperature obtained in each well may vary, when subjecting the microtiter plate to an oscillating magnetic field.

When the solid support member is a test tube, it is most preferred that the electrically conducting material is fixed on the inner side of the wall or loosely placed in the well in form of beads, powder, disk or sticks.

When the specimen is in a solid, semi-solid or high-viscous liquid form, or in the form of a cell suspension, and the carrier is a microscope slide or a similar plate, the solid support member may preferably be a cartridge or a cover plate for the microscope slide.

A useful cartridge may comprise at least one chamber encompassed by a cartridge wall, and one or more pieces of electrically conducting materials. In the heat control step, the microscope slide with the specimen is placed in the chamber, and the cartridge is subjected to an oscillating magnetic field. The chamber should preferably comprise at least one access opening for introducing the microscope slide, and for passing a processing fluid into and out of the chamber for treating the specimen. The conducting material may e.g. be in the form of a solid piece of conducting material placed on the inner side of the cartridge wall, or in the form of one or more solid pieces or particles of conducting material incorporated in the wall of said cartridge.

A useful cartridge may e.g. be selected among the cartridges described in U.S. Pat. No. 5,068,091, U.S. Pat. No. 5,338,358, WO 94/18539 or WO application No. PCT/DK98/00580 modified by incorporating an electrically conducting material. These cartridges are all adapted to be used in combination with either one or several microscope slides, on which slide or slides the specimen or specimens are placed. The slide or slides are inserted into the cartridge.

As indicated above, ir is preferred that the solid support member is a cartridge and that it is used in combination with at least one microscope slide, and more preferred a cartridge in combination with one microscope slide as the carrier. The cartridge comprises preferably a chamber for each slide which it is adapted to be combined with, and at least one access opening for introducing and withdrawing each of these slides. Furthermore, the cartridge comprises at least one opening for passing a processing fluid into and out of the chamber or chambers.

The electrically conducting material may be placed on, or incorporated into the cartridge. The electrically conducting material may e.g. be in the form of a solid piece of conducting material placed on the inner side of the cartridge wall or more solid pieces or particles of conducting material incorporated in the wall of the cartridge.

A particularly preferred cartridge in combination with one or more microscope slides as carrier is a cartridge in combination with a microscope slide, where the cartridge comprises a housing having a cavity therein and an aperture providing access for the introduction of the microscope slide into the cavity, so as to divide it in two compartments when the microscope slide is inserted therein. One of the compartments (called the first one) is defined by the sample bearing surface of the slide, an inner surface of the cavity and spacing means there between of such size, form and configuration that the dimension of the first compartment perpendicular to the sample bearing surface of the support member and the inner surface of the cavity is of capillary dimensions. The other compartment (called the second compartment) is defined by opposite surface(s) to the sample bearing surface of the slide and the remaining inner surface (s) of the cavity. The cavity is provided with elastical means engaging said support member and biasing the sample bearing surface of the support member against said spacing means in the first compartment. Tis cartridge is described in further details in WO application No. PCT/DK98/00580. This cartridge is further equipped with electrically conducting material e.g. in the form of a solid piece of conducting material placed on the inner side of the cartridge wall or more solid pieces or particles of conducting material incorporated in the wall of the cartridge. Most preferably the electrically conducting material is in the form of a solid piece of conducting material placed on the inner side of the cartridge wall of the first compartment. This first compartment cartridge wall comprises an opening allowing direct contact to the solid piece of conducting material for measuring the temperature of this material.

In another embodiment, the solid support member is constituted by a cover plate for a microscope slide.

When the solid support member is constituted by a cover plate for a microscope slide, the electrically conducting material may be placed on or incorporated into the cover plate. The slide may be a simple slide of glass, polymer or other electrically non-conducting materials. The cover plate may in principle have any shape e.g. a shape as a microscope slide which further comprises the electrically conducting material. Such sets of slides, but without electrically conducting materials, are described in U.S. Pat. No. 4,731,335, and the sets of slides in modified form (equipped with electrically conducting materials) as well as the slide holder may be used in the method of the present invention.

Alternatively, the cover plate may have any other shape provided that it comprises a surface adapted to cover a specimen on the surface of a carrier e.g. in the form of a microscope slide. A useful combination of a microscope slide and a cover plate which naturally should be modified (equipped with electrically conducting materials is e.g. described in WO 96/21142.

In all the above embodiments, including a microscope slide as carrier, it is preferred that the slide is a transparent slide, at least on the central part of the slide. Ordinary microscope slides of glass may preferably be used.

The electrically conducting material may be any type of material which is able to generate heat when subjected to an oscillating magnetic field. Preferred electrically conducting materials are non magnetic metals, more preferably a metal selected among iron, carbon steel, stainless steel, brass, copper, aluminium, silver, gold, platinum, nickel, zinc, pewter or alloys thereof. The electrically conducting material may preferably be in the form of a plate element e.g. a disk which is composed of two layers, a first layer of a highly inductive material e.g. iron, carbon steel or stainless steel, and a second layer of a highly heat conducting material e.g. copper, or silver. The layer of a highly heat conducting material should preferably be turned against the carrier. In a preferred embodiment the electrically conducting material is in the form of a plate element composed of two layers, a first layer of iron and a second layer of silver, wherein the layer of iron is relatively thick compared to the layer of silver e.g. 3–10 times thicker.

The electrically conducting material should preferably have a large surface, relative to the amount of electrically conducting material in order to provide a fast heat regulation, including allowing a fast cooling of the specimen. When the electrically conducting material is in the form of one or more pieces, this or these one or more pieces may be in the form of one or more plates, having a length, a width and a thickness wherein the length and the width, respectively, are at least 10 times the thickness.

The amount of electrically conducting material in a solid support depends on the type and size of the support as well as the type and size of specimen(s) and the choice of electrically conducting materials. In most situations, the solid support member preferably comprises between 10 and 100.000 mg of a conducting material. A skilled person may determine the optimal amount by carrying out a few tests.

When the electrically conducting material is in the form of powder incorporated into the material constituting the whole or a part of the solid support member, this material wherein the powder is incorporated, is preferably a polymer material e.g. as mentioned later on.

The amount of electrically conducting material should be sufficiently high to raise the temperature of the specimen when the solid support is subjected to the oscillating magnetic field.

Generally the carrier is preferably at least partly of a glass material or a polymer material. At least a part of the glass material or the polymer material in direct contact with the specimen is preferably transparent in order to make the specimen easily visible. The solid support member may preferably be partly of a glass material or a polymer material.

If the carrier is at least partly of a polymer material, this polymer material may in general be of any type of polymer that does not result in an unwanted interference with the specimen. The polymer material for the support member and the carrier may preferably be selected from synthetic and natural polymers such as polystyrene, polyethylene, polyurethane, polyethylene teraphthlates, polyvinylacetate, polyvinyl-chloride, polyvinyl-pyrrolidone, polyacrylonitrile, polymethyl-methacrylate, polytetrafluoro-ethylene, polycarbonate, poly-4-methyl-pentylene, polyester, poly-styrene polypropylene, cellulose, nitro-cellulose, starch, polysaccharides, natural rubber, butyl rubber, styrene butadiene rubber, silicone rubber and copolymers or mixtures thereof.

It is preferred that the magnetic field is generated by use of an electromagnetic inductor comprising an induction coil in the form of a wire wound into a coil with one or more windings, and a power supply sending alternating current through the coil. Such electromagnetic inductors are generally known to a skilled person. The electromagnetic inductor may have any shape, provided that it is able to generate an oscillating magnetic field, and that the solid support member can be placed in this oscillating magnetic field. The electromagnetic inductor should preferably be able to create a substantially homogenous field or a size which is at least sufficiently large to cover all of the electrically conducting material in a carrier. The size of the field generally depends on the shape of the inductor. The inductor may comprise a movable shelf surrounded by the coil, and on which shelf the solid support member or members may be placed. The movable shelf in the oscillating magnetic field may, when it is moved during the induction heating step, result in a more evenly distribution of the heat effect of the specimen(s) in the solid support member(s) placed on the shelf.

The power supply may be an A.C. power supply, the frequency range is between 50 Hz–500 kHz e.g. 133–215 kHz, preferably up to 200 kHz, and the power delivered through said coil is up to about 100 W, preferably between 5 and 75 W, e.g. about 15 or 20, more preferably between 25 and 50 W. If many specimens are to be heat controlled at the same time, the power delivered through said coil may be higher, e.g. up to about 1000 W.

In the method according to the invention, it is preferred that the specimen is a biological specimen. However, the method may in general be used for any type of biological, chemical and physical tests on organic and inorganic materials, preferably on organic materials.

The method is particularly useful for testing or treating vegetable or animal specimens, preferably human specimens e.g. cellular specimens of skin, bones, blood or muscles.

Any type of test procedures including a heat control step may be carried out using the claimed method. Examples of test procedures are described. Solid support members as described in the prior art publications U.S. Pat. No. 5,068,091, U.S. Pat. No. 5,338,358, WO publication 94/18539, WO application No. PCT/DK98/00580, WO publication No. 92/01919, WO publication No. 97/03827, U.S. Pat. No. 5,232,667, U.S. Pat. No. 5,244,787 and U.S. Pat. No. 5,023,187 may be used. Preferred procedures are immunohistochemical or/and in situ hybridisation.

In the method according to the invention, the step of heat control includes heating the specimen to a temperature of between 25 and 110° C., preferably between 30 and 95° C., more preferably between 35 and 85° C.

In another preferred embodiment, the specimen is heated and maintained at a constant temperature for a period of 1 minute and up to 1 week, preferably for up to 1 hour. The specimen may e.g. be incubated at 35° C. for 24 hours using this method.

The step of a procedure including heat control may also be drying, and/or fixing of the specimen at an elevated temperature (e.g. a temperature above 30° C.) or subjecting the specimen to a reaction step at an elevated temperature (e.g. a temperature above 30° C.). The reaction step may e.g. comprise capturing a specimen, baking the specimen (e.g. fixing of tissue onto a slide), exposing the specimen to antigen retrieval, denaturating the specimen, hybridisating the specimen, dewaxing (deparafinating) the specimen and washing the specimen.

The method according to the invention in its first aspect provides a fast and precise heat regulation of a specimen on a carrier with a very low risk of overheating the specimen, and furthermore the practitioner does not need knowing if the specimen should be subjected to a heating step or not prior to fixing the specimen onto the carrier. Thereby the method can be used in a very flexible manner and is easy to incorporate into normally used procedures.

The present invention in its first aspect also relates to the solid support member as well as the use of said solid support member as described in further details above.

The invention in its second aspect relates to a method for controlling the temperature of a specimen or a capture probe for a specimen with or without captured specimen fixed or immobilized onto one or more micro beads. The beads should have a size sufficiently small to be flowable in a liquid fluid, preferably water. Preferably, the beads should have an average size of between 1–1.000.000 nm, preferably 1000 to 100.000 nm, more preferably 25–10.000 nm.

The bead or beads may be partly or totally of an electrically conducting material. Preferably, the beads comprise a core of metal and a polymeric cover, wherein the core preferably may constitute 50 to 98 volume-% of the beads. The electrically conducting material may be as described above in the first aspect of the invention.

The specimen may be any type of specimen which can be fixed or immobilized onto the bead. Methods of fixing or immobilizing such specimen are well-known in the art.

The test including the heating step may be as described above for the first aspect of the invention.

The bead or beads are placed in a liquid e.g. a treatment liquid, and the method includes the step of carrying the one or more micro beads through an oscillating magnetic field for generating heat by use of a flow stream in the liquid. The oscillating field may be generated as described above for the first aspect of the invention.

Assays on beads in a flow system are generally known in the art. In a preferred method lyzed specimen is mixed with a mixture of a detection probe and the metal containing bead pre-coated with a specific capture probe or the lyzed specimen is mixed with a metal containing bead pre-coated with a specific molecular beacon. The specific probes can be selected by a person skilled in the art using normal and well-known procedures. The complete mixture is then carried through a flow system e.g. a flow cytometer, which contains an induction coil surrounding or close to the flow path, and located just prior to the detection system of the flow system. The beads are located inside the oscillating magnetic field generated by the induction coil for a sufficient time to heat the beads. The heat is used to insure that only specific capture is detected in the flow cell.

When the specimen has been treated with a liquid, the liquid may be separated from the beads carrying the specimen by capturing the beads with a magnet.

FIG. 3 shows a microtiter plate 11 in a perspective view.

FIG. 4 shows a test tube seen in cross-section.

FIG. 5 shows a microscope slide in combination with a cover plate in cross-section.

Figure 1:
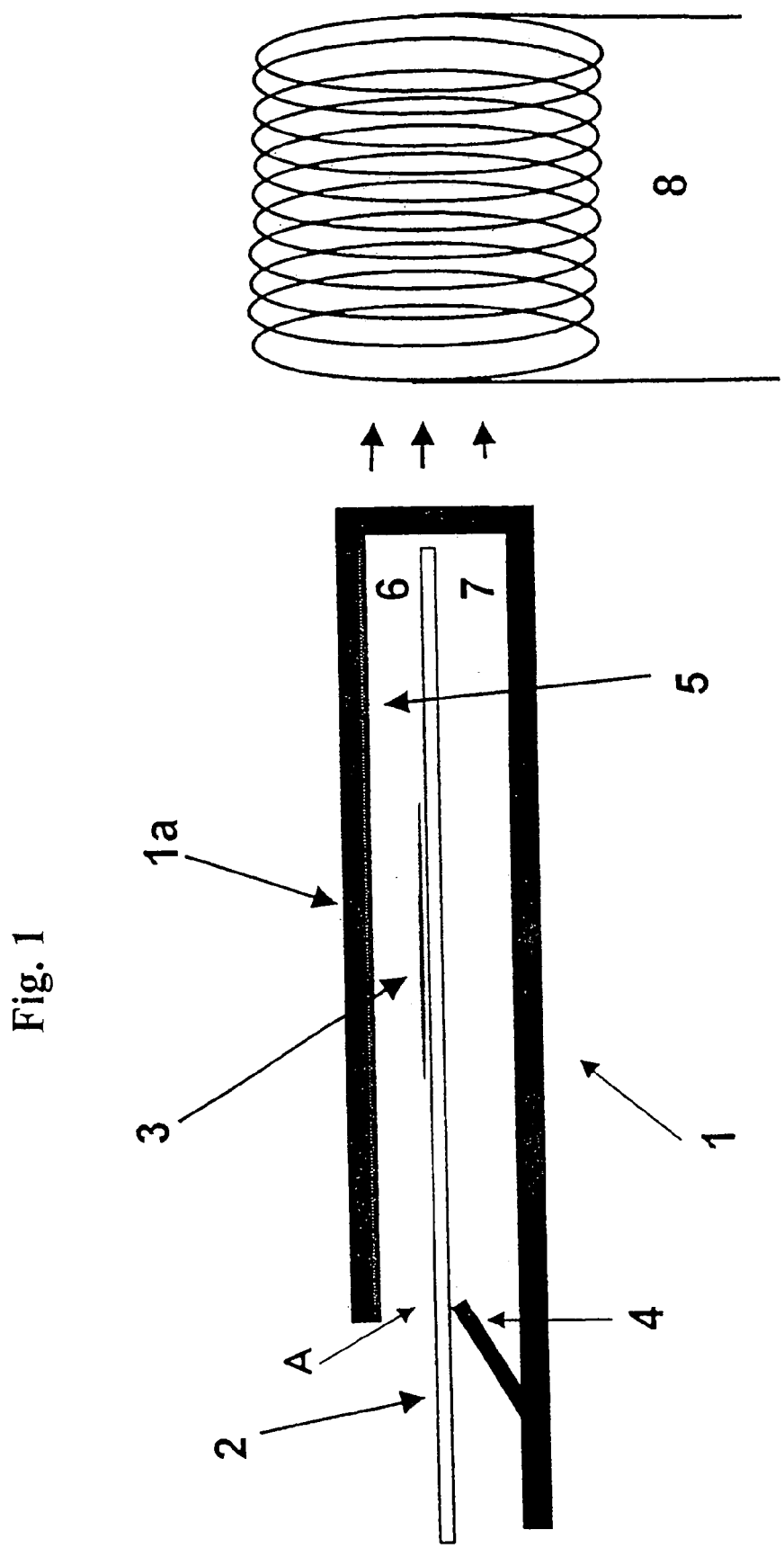
FIG. 1 shows a cartridge with a microscope slide in cross-section.

FIG. 1 shows a cartridge 1 with a traditional microscope glass slide 2 in cross-section. A specimen in the form of a tissue section 3 is fixed to the upper surface of the slide 2. The cartridge comprises a cavity, wherein the slide is introduced through access opening A. The cavity is divided into a first and a second compartment 6, 7. An elastically protruding flange 4 is placed in the bottom of the cartridge cavity in the second compartment. A metal membrane 5, preferably composed of carbon steel, is fixed in the upper sealing of the cavity. The upper wall of the cartridge has an opening 1a allowing direct access to the metal membrane for measuring the temperature of the metal. In use, a treatment liquid is introduced into the first compartment and the cartridge is introduced into an induction coil 8. When an oscillating magnetic field is created, the metal film will generate heat and the heat will be directly conducted to the specimen.

Figure 2:
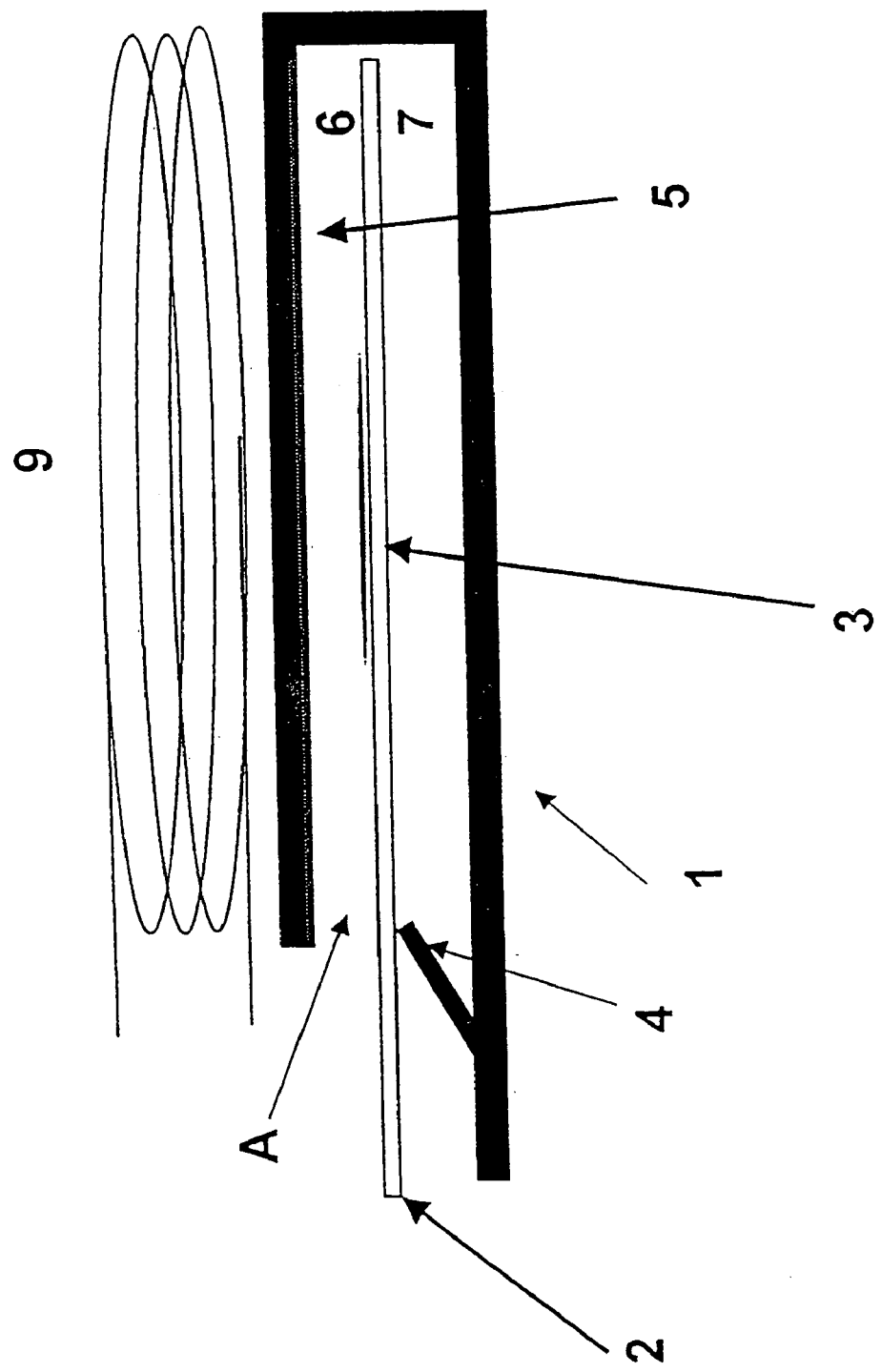
FIG. 2 shows a cartridge similar to the cartridge of FIG.

FIG. 2 shows a cartridge similar to the cartridge of FIG. 1. Above the cartridge 1 is placed an induction coil 9. When the first compartment is filled with treatment liquid and an oscillating magnetic field is created, the metal film will generate heat and the heat will be directly conducted to the specimen.

FIG. 3 shows a microtiter plate 11 in a perspective view. Only a number of the wells 12, 12' are shown. Some of the wells 12' of the microtiter plate comprise a metal piece 13 loosely placed onto the bottom of the wells. The substrate comprising the specimen may be an area of the walls of the wells or the substrate may be in the form of particles or beads, which are placed in the wells 12' together with a treatment liquid prior to the heat treatment step. Below the microtiter plate 11 is placed an induction coil 14. When the microtiter plate 11 is subjected to an oscillating magnetic field, heat is generated in the metal 13, and the specimen is heated to a preselected temperature.

FIG. 4 shows a test tube 27 seen in cross-section. The test tube has one well 28 comprising a not shown reaction medium e.g. comprising a cell suspension. A probe 21 comprising an electrically conducting material is inserted into the reaction medium. Capture probes are fixed to not shown beads which are also applied into the reaction medium. An electromagnetic induction coil 25 surrounds the test tube. When an oscillating magnetic field is created, the electrically conducting metal generates heat and the heat will be directly conducted to the capture probe whereby influencing the reaction between the capture probes and the cells.

FIG. 5 shows a microscope slide 32a in combination with a cover plate 32b. The microscope slide is an ordinary glass slide or a similar electrically non-conducting slide carrying a specimen 33 on its upper surface. The >cover plate is prepared from a similar slide, and comprises further a layer 35 of an electrically conducting metal on it surface turning against the first slide. The microscope slide and the cover plates are sandwiched with the specimen in between. An electromagnetic induction coil 38 is placed sufficiently close to the cover plates to be able to provide an oscillating magnetic field in the cover plate, which plate there generates heat, and the specimen is heated to a pre-selected temperature.

EXAMPLES

Example 1

A cartridge with a microscope slide as shown in FIG. 1 containing a carbon-steel membrane with a thickness of 0.05 mm as described above in FIG. 1 was filled with 500 $\mu$l water in the first compartment of the cartridge. The cartridge was placed on an induction coil capable of delivering a maximum of 600 W. Since the cartridge covered only 1/20 of the coil, the energy delivered to the cartridge is expected to be below 30 W. The initial temperature of the water sample in the cartridge was measured to 22° C. using a temperature sensor placed in the first compartment of the cartridge. The induction generator was turned on and the temperature followed. After 60 seconds, the temperature reached 72° C.

Example 2

A cartridge as shown in FIG. 1 with a 0.25 mm thick carbon-steel membrane was inserted into a surrounding induction coil (60 W). The first compartment of the cartridge was filled with 200 $\mu$l water. The water was heated with the induction coil to 80° C. in 20 sec and kept at this temperature using a temperature feedback device for 5 min. The heating was then discontinued, and the sample allowed cooling to room temperature.

Example 3

A cartridge as shown in FIG. 1 with a 0.25 mm thick carbon-steel membrane was inserted into a surrounding induction coil (20 W). The first compartment of the cartridge was filled with 200 $\mu$l water. The temperature of the water was followed by a sensor placed in the first compartment, and the temperature of the metal membrane was measured by an IR temperature sensor placed near the membrane above the opening 1a in the upper wall of the cartridge. The membrane was heated to 50° C. using the induction coil. After about 38 seconds the temperature of the metal plate was reached and this temperature of the membrane was held constant for 600 seconds using feedback control. The temperature of the water reached a temperature of about 48° C. after 80 seconds and this temperature was kept constant until the oscillating magnetic field was turned off.

Example 4

A traditional microscope slide with a specimen in the form of a fixed metaphase spread of human blood cell was first manually pre-treated with a proteolytic enzyme for 10 minutes and then the specimen was dehydrated with cold ethanol for 6 minutes. The slide was inserted into a cartridge as shown in FIG. 1. The metal membrane of the cartridge had a thickness of 0.25 mm and a width and length of about 2×3 cm. 200 $\mu$l probe mixture from the DAKO Telomere PNA FISH KIT (product No. K 5326) was added into the first compartment of the cartridge. The cartridge with the slide was inserted into an induction coil (20 W) equipped with a temperature control unit comprising an IR temperature sensor placed near the membrane above an opening in the upper wall of the cartridge. The membrane was heated to 80° C. within 150 seconds and was kept at this temperature for 3 minutes. The induction coil was turned off and the specimen was allowed cooling to room temperature for about 30 minutes. The remaining probe mixture was removed from the first compartment and the slide was washed at room temperature. Stringent wash was carried out using 3 times 200 $\mu$l wash buffer which in each wash was heated to 55° C. for 5 minutes by turning on the induction coil. Finally the slide was removed from the cartridge and dehydrated using cold ethanol. The dried specimen was mounted in antifade with DAPI according to the DAKO Telomere PNA FISH KIT. No sign of local overheating of the specimen could be observed. The result was equivalent to the fully manual procedure.

Example 5

Specimen was immobilized onto latex beads and added to each well of a microtiter plate together with water as shown in FIG. 3. The water was heated to 85° C. for 10 mm by induction heat and controlled by a temperature control device. No sign of local overheating of the specimen was observed.

Example 6

Beads with a metal core of 1 $\mu$m and a latex coating containing a capture probe was placed in a tube and incubated with a mixture of a complementary oligonucleotide labelled with FITC and a mismached oligonucleotide labelled with rhodamine. The beads were heated by applying an inductive field. Then the beads were fixed in the tube using an electro magnet, and the remaining components were poured out and washing buffer was added to the well. The beads were released from the magnet and thoroughly mixed into the washing buffer and stringently washed by applying a new round of induction field. The resulting particles were analysed by flow cytometry and florescence microscopy and it was verified that there was a clear discrimination between the complementary and the mismatched oligo target.

Example 7

A cartridge as shown in FIG. 1 with a 0.25 mm thick Fe membrane coated with 50 μm Ag on the inner surface i.e. the surface turning against the first compartment of the cartridge was inserted into a surrounding induction coil made up by 2 individual coils which together were capable of delivering up to 20 W. The first compartment of the cartridge was filled with 200 μl hybridization buffer. The temperature of the membrane as well as of the buffer was measured as described in example 3. The buffer was heated with the induction coils to 55° C. within less than 20 sec. after initiating the heat generation, and kept at this temperature for 300 sec. using a temperature feedback device. Within another 20 seconds the temperature was raised to 90° C. and kept at this temperature for 200 sec. The induction was turned of and during a period of 5 minutes the buffer was removed and new buffer added before the temperature was adjusted to 55° within 10 sec and kept at this temperature for another 300 sec. The temperature accuracy was determined to be within 3.

What is claimed is:

1. A method for controlling the temperature of a biological specimen in indirect contact with a solid support member by using induction heating and a carrier for a biological specimen, said carrier being removably placed in proximity to said solid support member, said solid support member includes a cartridge for said carrier or a cover plate for said carrier and comprising an electrically conducting material, said electrically conducting material being in contact with a layer of heat conducting material, said heat conducting material is in contact with the specimen, and said method comprising a step of subjecting said solid support to an oscillating magnetic field.

2. A method according to claim 1, wherein said solid support member includes a cartridge having a chamber encompassed by a cartridge wall, said carrier being placed in said chamber and said chamber being subjected to a magnetic field, said chamber includes at least one access opening for introducing the carrier, and for passing a processing fluid into and out of the chamber.

3. A method according to claim 2 wherein said conducting material includes the form of a solid piece of electrically conducting material placed on the inner side of said cartridge wall, or the form of one or more solid pieces or particles of electrically conducting material incorporated in the wall of said cartridge.

4. A method according to claim 2, wherein said carrier includes a microscope slide, said cartridge comprising a chamber, and at least one access opening for introducing and withdrawing said slide, and having at least one opening for passing a processing fluid into and out of the chamber, said microscope slide is placed in said chamber.

5. A method according to claim 1, wherein said carrier comprises a microscope slide bearing a specimen or capture probes for capturing a specimen said solid support member includes a cover plate for said microscope slide, said cover plate comprising an electrically conducting material, said specimen or said capture probes being fixed onto said microscope slide and placed between said cover plate and said slide when subjecting said solid support to an oscillating magnetic field.

6. A method according to claim 1, wherein the electrically conducting material includes a metal.

7. A method according to claim 6, wherein said metal is selected from a group consisting of iron, carbon steel, stainless steel, brass, copper, aluminum, silver, gold, platinum, nickel, zinc, pewter and alloys thereof.

8. A method according to claim 1, wherein the electrically conducting material is in the form of one or more plates, having a length, a width, and a thickness, said length and said width being at least ten times the thickness.

9. A method according to claim 1, wherein the electrically conducting material is in the form of powder incorporated in a polymer material, the amount of powder being sufficiently high to raise the temperature of the specimen when the solid support is subjected to the oscillating magnetic field.

10. A method according to claim 9, wherein said specimen is in the form of a solid specimen, preferably a tissue section or a section of cell blocks.

11. A method according to claim 1, wherein said solid support includes an amount of electrically conducting material sufficiently high to raise the temperature of the specimen when the solid support is subjected to the oscillating magnetic field.

12. A method according to claim 1, wherein said magnetic field is generated by use of an electromagnetic inductor having an induction coil and a power supply, and directing alternating current through said coil.

13. A method according to claim 12, wherein said power supply includes an alternating current power supply.

14. A method according to claim 12, wherein said alternating current power includes a frequency in the range of between 1 Hz and 500 kHz.

15. A method according to claim 12, wherein alternating current is delivered through said coil in an amount of power up to about 100 W.

16. A method according to claim 1, comprising a step of heating the specimen to a temperature in the range of between 25 and 110° C.

17. A method according to claim 1, wherein the specimen is heated and maintained at a constant temperature for a period in the range of between one minute and up to one week.

18. A method according to claim 1, wherein the specimen is dried or fixed or both at an elevated temperature.

19. A method according to claim 1, wherein the specimen is subjected to a reaction step at an elevated temperature, said reaction step includes one or more of the steps capturing the specimen, baking the specimen, exposing the specimen to antigen retrieval, denaturing the specimen, hybridizating the specimen, dewaxing the specimen and washing the specimen.

20. Use of the method according to claim 1 for treatment of a biological specimen.

21. Use of the method according to claim 1 for immunohistochemical procedures or in situ hybridization.

22. A method for carrying out an automatic or semi-automatic assay of one or more specimens each fixed on a microscope slide, comprising the steps of:

i) placing the microscope slide in a cartridge comprising a chamber encompassed by a cartridge wall having an inner side, said cartridge comprising an electrically conducting material in the form of a solid piece of conducting material placed on the inner side of said cartridge wall, or in the form of one or more solid pieces or particles of conducting material incorporated in the wall of said cartridge; and ii) placing the cartridge in an induction coil and sending alternating current through said coil to generate a magnetic field.

23. A method according to claim 22 including an automatic or semi-automatic assay of two or more specimens, comprising the additional steps of:
  iii) placing each microscope slide individually in a cartridge including a chamber encompassed by a cartridge wall, said cartridge comprising an electrically conducting material in the form of a solid piece of conducting material placed on the inner side of said cartridge wall, or in the form of one or more solid pieces or particles of conducting material incorporated in the wall of said cartridge; and
  iv) placing each cartridge individually in an induction coil and sending alternating current through said coil to generate a magnetic field.

24. A method for controlling the temperature of a biological specimen while testing or treating said biological specimen by employing a solid support member in combination with a carrier and an electromagnetic inductor, said inductor, comprising electrically conducting material on the surface facing the side of the carrier carrying the specimen, and generating a magnetic field with said electromagnetic inductor in the presence of the biological specimen.

25. The method for controlling the temperature of said biological specimen by employing solid support member in combination with an inductor according to claim 24, wherein said inductor comprises an induction coil and a power supply, said coil, preferably being sufficiently large to surround the support member, and said power supply capable of sending alternating current through said coil.

26. The method for controlling temperature according to claim 25, wherein said power supply includes an AC power supply.

27. A solid support member in combination with a carrier and an electromagnetic inductor for controlling the temperature of a specimen in direct or indirect contact with a solid support member by using induction heating, said support member being a cartridge for the carrier (e.g. a microscope slide) support member for testing or treating a specimen of biological material, and said support member comprising electrically conducting material on the surface facing the side of the carrier carrying the specimen and said electromagnetic inductor capable of generating an oscillating magnetic field to cause induction heating in the electrically conducting material of the support member.

28. A solid support member in combination with an inductor according to claim 27, wherein said inductor comprises an induction coil and a power supply, said coil being sufficiently large to surround the support member and said power supply being able to send alternating current through said coil.

29. A solid support member according to claim 27 wherein said power supply includes an AC power supply.

30. A solid support member according to claim 29 wherein said AC power supply includes a frequency in the range of between 1 Hz and 500 kHz.

31. A solid support member in combination with a carrier and an electromagnetic inductor for controlling the temperature of a specimen in direct or indirect contact with a solid support member providing induction heating, said support member being a cover plate for a microscope slide support member for testing or treating a specimen of biological material, and said support member comprising electrically conducting material on the surface facing the side of the carrier carrying the specimen and said electromagnetic inductor being able to generate an oscillating magnetic field, causing induction heating in the electrically conducting material of the support member.

* * * * *